United States Patent [19]

Miller

[11] Patent Number: 5,266,468
[45] Date of Patent: Nov. 30, 1993

[54] PROCESS FOR PREPARING β-HYDROXY-α AMINO ACIDS

[75] Inventor: Marvin J. Miller, South Bend, Ind.

[73] Assignee: University of Notre Dame du Lac, Notre Dame, Ind.

[21] Appl. No.: 918,878

[22] Filed: Jul. 22, 1992

Related U.S. Application Data

[63] Continuation of Ser. No. 827,556, Jan. 28, 1992, abandoned, which is a continuation of Ser. No. 532,845, Jun. 4, 1990, abandoned.

[51] Int. Cl.$^5$ .................. C12P 13/04; C07C 215/00
[52] U.S. Cl. .................................. 435/106; 564/503
[58] Field of Search .................................. 435/106

[56] References Cited

U.S. PATENT DOCUMENTS

| | | | |
|---|---|---|---|
| 3,871,958 | 3/1975 | Nakazawa et al. | 435/106 |
| 4,710,583 | 12/1987 | Chmurny et al. | 435/68.1 X |
| 4,782,021 | 11/1988 | Ishiwata et al. | 435/106 X |
| 5,102,792 | 4/1992 | Walter et al. | 435/116 |

FOREIGN PATENT DOCUMENTS

| | | | |
|---|---|---|---|
| 165044 | 12/1985 | European Pat. Off. | 435/106 |
| 52-51094 | 4/1977 | Japan . | |
| 58-116690 | 7/1983 | Japan . | |
| 1-317391 | 12/1989 | Japan . | |
| 2-42994 | 2/1990 | Japan | 435/106 |
| 2130216A | 5/1984 | United Kingdom . | |

OTHER PUBLICATIONS

Webb, EC *Enzyme Nomenclature* 1984 pp. 154–155.
Reno, D. S. et al., Tetrahedron Letters, vol. 31, No. 6, pp. 827–830, 1990.
Jung, M. and Miller, M. J., Tetrahedron Letters, vol. 26, No. 8, 977–980, 1985.
Schirch, LaVerne, J. of Biol. Chem., vol. 237, No. 8, Aug. 1962, 2578-81.
Schirch, LaVerne, Methods of Enzymology, vol. 17, Pt B, pp. 335–340.

*Primary Examiner*—David M. Naff
*Assistant Examiner*—Deborah Hung
*Attorney, Agent, or Firm*—James J. Sales; Leroy Whitaker

[57] ABSTRACT

β-Hydroxy-α-amino acids are obtained via serine hydroxymethyltransferase catalyzed condensation of aldehydes with glycine. The predominant product with most aldehydes is the L-erythro diastereomer. For example, succinic semialdehyde methylester is condensed with glycine in the process to provide L-erythro α-amino hydroxy adipic acid mono methyl ester.

3 Claims, No Drawings

PROCESS FOR PREPARING β-HYDROXY-α AMINO ACIDS

This is a continuation of Ser. No. 07/827,556, filed Jan. 28, 1992, now abandoned, which is a continuation of Ser. No. 07/532,845, filed Jun. 4, 1990, now abandoned.

BACKGROUND OF THE INVENTION

This invention relates to a process for preparing β-hydroxy-α-amino acids. In particular it relates to an enzymatic process for preparing β-hydroxy-α-amino acids substantially in the L-erythro-form.

The β-hydroxy-α-amino acids have many uses including use as intermediates in the preparation of β-lactam antibiotics. See, for example, Mattingly, P. G.; Miller, M. J., J. Org. Chem. 1981, 46, 1557 and Miller, M. J., et al. J. Am. Chem. Soc. 1980, 102, 7026. A number of chemical methods for the preparation of β-hydroxy-α-amino acids are known, however, most have one or more disadvantages. These include a lack of generality, poor stereochemical control, requirement of chiral auxiliaries, or production of primarily the threo (or syn) isomers.

Enzymatic processes have some distinct advantages over chemical processes. For example, they are carried out in aqueous systems under mild conditions and, frequently are stereoselective. The enzyme employed in the process of the invention is known generally as an aldolase. One such aldolase is serine hydroxymethyltransferase (SHMT), Schirch, L. Adv. Enzymol. Relat. Areas Mol. Biol. 1982, 53, 83 and Schirch, L.; Gross, T. J. Biol. Chem. 1968, 243, 5651. The natural biological roles of the aldolases involve the transfer of one-carbon units to or from serine and the retroaldol cleavage of β-hydroxy-α-amino acids such as threonine and allothreonine to generate an aldehyde and glycine.

The aldolases are ubiquitous in plants, bacteria and animals, for example, corn seedlings, mung bean seedlings, and rabbit liver. The process of this invention comprises the use of SHMT to elaborate, under mild conditions, β-hydroxy-α-amino acid precursors to β-lactam antibiotics. The process provides in numerous instances the β-hydroxy amino acid in the L-erythro isomeric form which is the desired from of the precursor providing the correct diastereomeric form of the β-lactam antibiotic.

SUMMARY OF THE INVENTION

The invention provides an enzymatic process for preparing β-hydroxy-α-amino acids which comprises incubating in an aqueous medium at a pH of between about 7 and about 8 and at a temperature of about 30° C. to about 55° C., glycine and an aliphatic aldehyde e.g. acetaldehyde or butanal or an aromatic aldehyde e.g. 2-furfural, with serine hydroxymethyltransferase (SHMT). For example, an ester of succinic semialdehyde is converted in the process to β-hydroxy-α-aminoadipic acid mono ester.

DETAILED DESCRIPTION

The process provided herein for the preparation of β-hydroxy-α-amino acids represented by the formula 1.

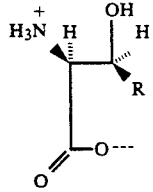

comprises mixing in an aqueous medium at a pH of between about 5.5 and about 9 glycine and an aldehyde RCHO in the presence of serine hydroxymethyltransferase and pyridoxal 5'-phosphate. The process is carried out at a temperature between about 30° C. and about 55° C. and preferably at about 37° C.

The relative proportions of glycine and the aldehyde RCHO may vary however, it appears that higher yields of product are obtained when equimolar amounts are used. The amount of enzyme used depends upon the extent to which the enzyme has been purified and the effect any impurities present may have on enzymatic activity.

The pH of the reaction medium is buffered at a pH between about 5.5 and about 9 and, with most substrates, preferably at a pH of between 7.0 and about 8.0. Phosphate buffers are suitable for providing the desired pH range.

As with other enzymatic reactions cofactors can influence the substrate specificity of the enzyme as well as the efficiency of the enzyme in catalyzing the reaction of a given substrate. An essential cofactor for the serine hydroxymethyltransferase in the process is pyridoxal 5'-phosphate. Other cofactors in addition to PLP which can be added have a beneficial effect on the yield of product obtained with some substrates. For example, tetrahydrofolic acid enhances the activity of the enzyme in converting the substrate pyruvaldehyde. Also, sodium metavanadate serves as a cofactor for the conversion of the same aldehyde.

The above formula 1 depicts the β-hydroxy-α-amino acids provided by the process in the inner salt form. This salt form is that expected at the pH of the process however the non-ionic form represented by the formula

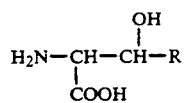

can also exist under other conditions.

The aldehyde, RCHO, employed in the process can be a straight or branched chain alkyl, alkenyl or alkynyl aldehyde or an aromatic or heterocyclic aldehyde. The aldehyde can bear substituent groups, for example, alkoxy such as methoxy or ethoxy, esterified carboxy such as $C_1$-$C_4$ alkyl esters of the carboxy group; cyano; hydroxy; acylated hydroxy such as formyloxy, acetoxy, propionoxy, or butyloxy; halogen such as fluoro or chloro; haloalkyl such as trifluoromethyl or chloromethyl; or the aliphatic aldehyde can contain oxo groups e.g. RCHO can be a ketoaldehyde such as 4-oxopentanal or pyruvaldehyde and the like. The aromatic aldehyde or heterocylic aldehyde can likewise be substituted on the aromatic or heterocyclic ring or on any alkyl or alkenyl portion thereof. Examples of alkyl, alkenyl and alkynyl aldehydes RCHO which can be used in the process are acetaldehyde, propionaldehyde, butyraldehyde, valeraldehyde, succinic semialdehyde methyl ester, succinic semialdehyde benzylester, 4β-hydroxyvaleraldehyde, glutaric semialdehyde methyl ester, pyruvaldehyde, O-formyl 4-hydroxyvaleraldehyde, 3-fluorovaleraldehyde, 5-chlorovaleraldehyde, 2-chloropropionaldehyde, propargyl aldehyde, and alkene aldehydes represented by the formulas

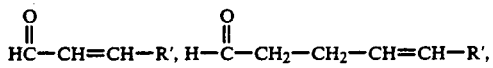

wherein R' is hydrogen or $C_1-C_4$ alkyl such as acrolein, crotonaldehyde and 4-pentenal.

Examples of aromatic and heterocyclic aldehydes RCHO for use in the process are benzaldehyde, tolualdehyde, anisaldehyde, veratrylaldehyde, phenylacetaldehyde, 3-phenylpropionaldehyde, 2-phenylpropionaldehyde, furfural, 2-(2-furyl)acetaldehyde, 3-furylacrolein, 3-phenylacrolein, 2-thiophenealdehyde, 3-(2-thienyl)acrolein, 3-(methoxyphenyl)acrolein, and like aromatic aldehydes.

Preferably, in the process of the invention R of the formula 1 is $C_2-C_6$ alkenyl, $C_2-C_6$ alkynyl, or $C_1-C_6$ alkyl substituted by esterified carboxy, $C_1-C_4$ alkanoxyloxy, or a $C_1-C_6$ alkyl group substituted by arylalkoxy. As used herein the term $C_2-C_6$ alkenyl refers to straight and branched unsaturated hydrocarbon chains such as ethenyl, propenyl, butenyl, pentenyl and hexenyl; $C_2-C_6$ alkynyl refers to ethynyl, propynyl, butynyl, pentynyl and hexynyl groups which may be branched; $C_1-C_6$ alkyl substituted by esterified carboxy refers to a straight and branched chained alkyl groups substituted by an esterified carboxy group wherein the ester group is $C_1-C_4$ alkyl, phenyl, benzyl, substituted benzyl such as p-methoxybenzyl, methylbenzyl, p-nitrobenzyl, diphenylmethyl, or other conventional carboxy protecting group. Examples of such groups are ethoxycarbonylmethyl, 2-(methoxycarbonyl)ethyl,3-(t-butyloxycarbonyl)propyl, 3-(benzyloxycarbonyl)butyl, 5-(4-methoxybenzyloxycarbonyl)hexyl, and like alkyl groups substituted by esterified carboxy groups. The term $C_1-C_6$ alkyl substituted by $C_1-C_4$ alkoxy refers to methoxymethyl, 2-ethoxyethyl, 4-t-butyloxybutyl, 3-isopropoxypentyl, 2-ethoxyhexyl and the like; $C_1-C_6$ alkyl substituted by fluoro or chloro refers to such groups as 2-fluoroethyl, 2-chloroethyl, 4-chlorobutyl, 5-chloropentyl, chloromethyl, fluoromethyl, 3-chloro-4-methylpentyl and the like; $C_1-C_6$ alkyl substituted by cyano refers to cyanomethyl, 2-cyanoethyl, 4-cyanobutyl, 3-cyanobutyl, 5-cyanohexyl and the like; $C_1-C_6$ alkyl substituted by hydroxy refers to hydroxymethyl, 2-hydroxymethyl, 4-hydroxybutyl, 3-hydroxypropyl, 3-hydroxyhexyl, and like group; $C_1-C_6$ alkyl substituted by $C_1-C_4$ alkanoyloxy refers to such groups as 2-acetoxyethyl, 2-formyloxyethyl, 3-acetoxypropyl, 4-propionoxybutyl and like groups; and $C_1-C_6$ alkyl substituted by arylalkoxy refers to benzyloxymethyl, diphenylmethoxymethyl, 4-benzyloxybutyl, 2-(4-methoxybenzyloxy)ethyl, 3-diphenylmethoxypropyl, and like groups.

Especially preferred aldehydes for use in the process are represented by RCHO wherein R is an alkene aldehyde

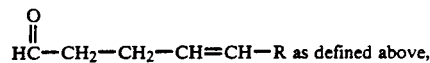

or $C_1-C_4$ alkyl substituted by an esterified carboxy group or a $C_1-C_4$ alkanoyloxy group. Examples of such groups are 2-(methoxycarbonyl) ethyl, 2-(benzyloxycarbonyl)ethyl, 3-(ethoxycarbonyl)propyl, 2-(formyloxy)ethyl and 2-acetoxyethyl.

The aldehydes, RCHO, used in the process are all known compounds available commercially or preparable by conventional methods. A preferred process of the invention comprises the use of the aldehyde RCHO wherein R is 2-(esterified carboxy)ethyl, 2-cyanoethyl, 2-(esterified carboxy)ethynyl, 2-(esterified carboxy)vinyl, 3-(esterified carboxy)propyl, 2-formyloxyethyl, 2-acetoxymethyl, 3-formyloxypropyl, or 3-acetoxypropyl, wherein the ester moiety of the esterified carboxy group is $C_1-C_4$ alkyl e.g. methyl, ethyl or t-butyl; phenyl, benzyl, diphenylmethyl, trityl or substituted benzyl e.g. 4-methoxybenzyl or 4-nitrobenzyl. An especially preferred aldehyde for use in the invention is succinic semialdehyde ester. Another especially preferred aldehyde is an ester of glutaric semialdehyde.

The following diagram depicts the reaction carried out in the process of this invention.

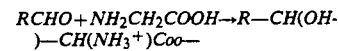

wherein R is as defined hereinabove.

As described above the serine hydroxymethyltransferase is available from a number of sources. Three such sources are rabbit liver (LaVerne Schirch and Merle Mason, J. Biol. Chem., Vol. 237, No. 8, August 1962), corn seedlings (Masuda, T., et al., Agric Biol. Chem. 1986, 50, 2763), and mung bean seedlings (Rao, D. N. and Rao, N. A., Plant Physiol. 1982, 69,11).

The following Table 1 lists representative aldehyde substrates which were converted in the process to β-hydroxy-α-amino acids with SHMT from two sources. The conversion of the substrates in Table 1 was carried out by incubating the substrate and glycine with SHMT under the conditions of the process. A number of the process conditions used were common to all of the substrates and are detailed in the following paragraphs. Wherever exceptions occurred they are noted in each instance.

The incubations were carried out in 10 mM phosphate buffer, pH 7.3 containing pyridoxal 5'-phosphate at a concentration of about 80 µM. All solutions were prepared from distilled, deionized water for best results. The conversions were carried out at about 37° C. in sealed, 500 L polypropylene microcentrifuge vials in a constant-temperature water bath. The vials were protected from light except when removed from the water bath for removal of aliquots for analysis. With all conversions an enzyme blank incubation was carried out in parallel with the SHMT incubation. The total volume of the incubation mixture was typically about 200 µL. The conditions in the blank were identical to those of the incubation mixture except for the absence of the enzyme.

TABLE 1
Aldehyde (RCHO) Substrates for SHMT

| Aldehyde (RCHO) R = | Enzyme[1] Rabbit Liver | Corn Seedlings |
|---|---|---|
| —$CH_3$ | + | + |
| —$CH_2CH_2CH_3$ | + | ND |
| —$CH_2CH_3$ | ND | + |
| —$CH_2CH_2CO_2CH_3$ | + | + |
| —$CH_2CH_2CO_2CH(CH_3)_2$ | + | ND |
| —$CO_2H$ | − | − |
| —$CH_2CH_2CH_2CO_2CH_3$ | + | + |
| —$C(O)CH_3$[2] | + | + |
| —$CH_2CH_2CH_2OCHO$ | + | ND |
| $C_6H_5$ | + | − |
| —$CH_2OCH_2C_6H_5$ | ND | + |
| 2-furyl | + | + |
| 2-(2-furyl)ethyl | + | − |

The process can be monitored for production of the β-hydroxy-α-amino acid by removing aliquots from the incubation mixture from time to time and assaying the samples by HPLC separation and fluorescence detection of o-phthalaldehyde derived idoindoles of all primary amine compounds present in the mixture. The assay procedure is described by Jones, B. N.; Gilligan, J. P., J. Chrom. 1983, 266, 471; Jones, B. N. et al., J Liq. Chrom. 1981, 4,565, and Simons, Jr., S. S. et al., J. Am Chem. Soc. 1976, 98, 7098. HPLC analysis of both the incubation mixture and the enzyme blank allowed determination of which peak(s) on the chromatograms could be assigned to enzyme products.

The process of the invention is carried out by adding the aldehyde to a buffered solution of glycine containing PLP and another cofactor and then mixing the solution with a buffered solution of the enzyme. Alternately, the buffered PLP-containing solution of glycine and the enzyme solution are mixed and the aldehyde is then added. It is also possible to add the enzyme solution to a solution of the aldehyde and glycine in the presence of the PLP-containing buffer.

It is not necessary that the aldehyde, RCHO, be completely in solution for its conversion to occur in the process. Aldehydes which are only partially soluble in the aqueous reaction medium also serve as substrates for the enzyme.

The process of the invention wherein the aldehyde, RCHO, is an aliphatic aldehyde (i.e. the carbon attached to the carbonyl group of the aldehyde function is saturated, $CH_2$,) provides preferentially the L-erythro diastereomer of the β-hydroxy-α-amino acid or ester. However, when the aldehyde substrate is aromatic (i.e. the carbon attached to the carbonyl of the aldehyde function is part of an aromatic system) the product is obtained in both the threo and erythro forms in about equal amounts. For example, benzaldehyde forms both the threo and erythro isomers of β-phenylserine.

Examples of β-hydroxy-α-amino acids obtained in the process of the invention are -phenylserine, β-(2-furyl)serine, β-hydroxy-α-aminoadipic acid, β-hydroxy-α-aminohexanoic acid, β-hydroxy-α-amino-ω-formyloxyhexanoic acid, β-hydroxy-α-amino-γ-oxovaleric acid, β-hydroxy-α-amino-γ-phenylbutyric acid, β-hydroxy-α-aminoheptanoic acid, β-hydroxy-α-amino-ω-(2-furyl)-pentanoic acid, and like amino acids.

In a preferred embodiment of the process an ester of succinic semialdehyde such as a $C_1$–$C_4$ alkyl ester e.g. the methyl ester or isopropyl ester is incubated with glycine and SHMT in phosphate buffer in the presence of PLP to yield the half ester of β-hydroxy-α-aminoadipic acid as the L-erythro isomer. In another preferred embodiment of the process an ester of glutaric semialdehyde, e.g. the methyl ester, is incubated with SHMT to provide the half ester of β-hydroxy-α-aminopimelic acid.

The foregoing two embodiments of the invention are illustrated in the following reaction scheme.

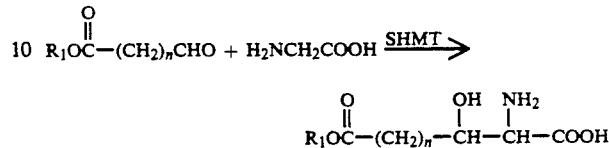

wherein $R_1$ is $C_1$–$C_4$ alkyl, phenyl, benzyl, diphenylmethyl, 4-methoxybenzyl or 4-nitrobenzyl and n is 2 or 3.

This invention further provides the amino acid, β-hydroxy-α-aminoadipic acid, the mono- and di-$R_1$ esters and salts thereof represented by the formula $R_1OOOC—CH_2—CH_2—CH(OH)CH(NH_2)COOR_1'$, wherein $R_1$ is defined above and $R_1'$ is hydrogen or $R_1$. This amino acid is obtained in the process in the L-erythro form. Salts of the diacid or mono ester thereof can be formed by conventional means. Such salts include the alkali metal salts such as the sodium and potassium salts, the alkaline earth metal salts such as the calcium salt, and the ammonium salts and amine salts such as are formed with benzylamine, dibenzylamine, cyclohexylamine, dicyclohexylamine, $C_1$–$C_4$ alkyl primary and secondary amines such as methylamine, ethylamine, diethylamine, di-(n-butyl)amine, ethanolamine, diethanolamine, dipropanolamine, and like salts. Such salts are useful in the isolation and purification of the diacid or a mono-ester thereof and provide stable forms for storage of the amino acid. Also provided are the acid addition salts formed with the amino acid and esters thereof. Such salts are formed with acids which are stronger than the acidic carboxylic acid groups of the amino acid. Examples of such acids are hydrochloric, hydrobromic, phosphoric and sulfuric acids, and the sulfonic acids such as toluenesulfonic acid, naphthalenesulfonic acid, methanesulfonic acid and n-butanesulfonic acid.

The $R_1$ esters thereof refers to the mono- and diesters wherein $R_1$ has the same meanings as defined above in the reaction scheme. Examples of such esters are the mono-methyl, mono-ethyl, dimethyl, diethyl, t-butyl, and di-t-butyl, benzyl, 4-methoxybenzyl and the dibenzyl esters thereof.

The β-hydroxy-α-amino acids provided by the process of this invention are useful intermediates to important β-lactam compounds. The products are converted by known methods to β-lactam compounds which are useful in the preparation of known antibiotic compounds. For example, the β-hydroxy-α-amino acids are converted to hydroxamate derivatives and the latter cyclized to form 3-amino-4-substituted β-lactam compounds as shown in the following reaction scheme

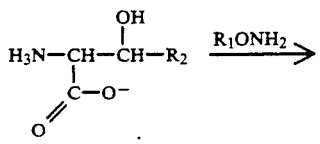

-continued

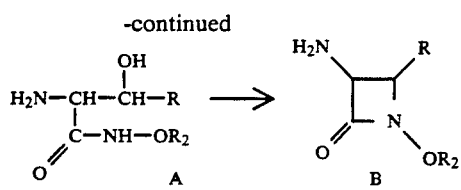

wherein R has the same meanings as defined above and for formula 1 and $R_2$ is an alkyl, alkanoyl or aralkyl group. The formation of the hydroxamate and the cyclization of the hydroxamate to the β-lactam is carried out by the method described by Miller, M. J. Accts. Chem. Res. 1986, 19, 49; Rajendra, G. and Miller, M. J. Tetrahedron Lett., 1987, 28, 6257; and Kolasa, T. and Miller, M. J. Tetrahedron Lett., 1987, 28, 1861.

Alternatively, the β-hydroxy-α-amino acids can be converted to N-(substituted methyl) azetidinones as described by Miller, M. J., U.S. Pat. No. 4,595,532. Further, still, the amino acid products of the process can be converted to the N-(phosphonomethyl) azetidinones described by Miller, M. J. U.S. Pat. No. 4,820,815.

The following preparations and examples further describe the process of the invention and are not intended to be restricted thereto.

Preparation of Serine Hydroxymethyltransferase from Corn Seedlings

All of the following procedures were carried out at 4° C. Washed 5-7 day old corn seedlings were homogenized in a Waring blender in 100 mM potassium monohydrogen phosphate containing 1 mM disodium ethylenediaminetetraacetate (EDTA), 1 mM dithiothreitol, and 125 μM of pyridoxal 5'-phosphate. The mix contained approximately 960 g of seedlings per liter. The homogenate was filtered through cheese cloth and the filtrate was subjected to ammonium sulfate precipitation. The protein which precipitated with 35-50% saturation in ammonium sulfate upon centrifuging at 13,800×g for 40 min. was dissolved in 10 mM phosphate buffer, pH 7.8, containing 125 μM pyridoxal 5'-phosphate and 1 mM EDTA. The solution was dialyzed and concentrated to 5-15 mg of protein/ml in the same buffer without EDTA present. Assay for aldolase activity of the protein consisted of a coupled system between the aldolase-catalyzed retroaldol of L-allo-threonine with the NADH (reduced form of nicotinamide adenine dinucleotide) dependent reduction of the resulting acetaldehyde by yeast alcohol dehydrogenase (ADH). Specific activity averaged 78 milliunits/mg of protein. One unit of enzyme activity is defined as that amount of enzyme required to cause a change of one optical density unit (at 340 nm) per minute at room temperature in the presence of ADH, 120 mM L-allo-threonine, 125 μM PLP, and 120 μM NADH in 100 mM phosphate buffer, pH 7.5.

The SHMT when not used when prepared was stored either in lyophilized form or frozen with 10% glycerol.

In the following examples, unless otherwise indicated, the buffer system was 10 mM potassium phosphate, pH 7.3, and contained pyridoxal 5'-phosphate (PLP) at a concentration of about 80 μM. All solutions were prepared in distilled, deionized water.

Incubations with the enzyme were carried out at 37° C. in sealed, 500 μL polypropylene microcentrifuge vials in a constant-temperature water bath.

The retention times given in the examples may vary slightly from time to time on HPLC analysis because of slight variations in such factors as column, equilibration, buffers and the like.

The SHMT employed in the following examples was obtained from rabbit liver, by L. Schirch (supra).

EXAMPLE 1

Preparation of Threonine

A solution of glycine (34 mM) was prepared in the PLP-containing phosphate buffer, and sufficient freshly distilled acetaldehyde was added to make its concentration also 34 mM. When added to the enzyme solution, the concentration of each substrate was 17 mM.

A solution of SHMT (0.1 mg) in 200 μL of the standard phosphate buffer was placed into a 2 mL glass vial. An equal volume of the substrate solution was added and the vial was sealed with a rubber septum and copper wire to minimize loss of acetaldehyde. This vial and an enzyme blank solution were incubated at 37° C.

Aliquots (10 μL) were removed via 50 μL microliter syringe at incubation times of 1.0, 2.0, 3.0, 4.0, and 20.5 hours and anlyzed by HPLC.

The chromatogram showed the major peak for the L-erythro isomer at 21.9 minutes retention time and a minor peak for the threoisomer. The identity of the amino acids produced was confirmed by co-injection with authentic commercially available threonine isomers.

EXAMPLE 2

α-Amino-η-hydroxycaproic acid

A substrate solution was prepared by dissolving glycine (25.5 mg. 0.340 mmol) and n-butanal (25.3 mg. 0.351 mmol) in 10 mL of the standard phosphate buffer, giving 34 mM and 35 mM concentrations of the two substrates, respectively.

A solution of SHMT (0.1 mg) in 100 μL buffer was placed in a 0.5 mL polypropylene vial. Another 100 μL of buffer without enzyme was placed into another vial, and 100 μL of the substrate solution was added to each vial.

Aliquots were taken from the enzyme and blank solutions at incubation times of 1.0, 3.0, 7.25, and 21 hours and analyzed by HPLC.

Two product peaks were seen in the chromatograms, a large one at 25.7 minutes and a small one at 24.3 minutes. The peaks corresponded to those from authentic, racemic product. The authentic material was made racemically by performing an aldol reaction on a copper complex of glycine, S. Akabari et al., *Archives of Biochemistry and Biophyisics* 1959, 83, 1, and J. P. Greenstein and M. Winitz, "Chemistry of Amino Acids," John Wiley & Sons, New York, 1961, Vol. 3, pp 2249-2250.

EXAMPLE 3

α-Amino-β-hydroxyadipic acid monomethyl ester

Glycine (13.3 mg. 0.177 mmol) and succinic semialdehyde methyl ester (20 mg, 0.172 mmol) were dissolved in 5.0 mL buffer to give 35 mM and 34 mM concentrations of each, respectively. The aldehyde used in this experiment was free of DMSO, although previous incubations with this aldehyde still contained the impurity (left over from its synthesis by ozonolysis of $CH_2=CH-CH_2-CH_2-COO-CH_2$ followed by workup with dimethylsulfoxide).

To a solution of SHMT (0.1 mg) in 100 μL buffer was added 100 μL of the substrate mixture. Aliquots were taken at incubation times of 0.5, 1.0, 2.0, 3.0, and 24 hours.

The major product peak (L-erythro) was observed at $t_R$ of 22.5 min. and reached its maximum at two hours.

During the initial two hours a small new peak appeared in the HPLC analysis with a retention time of approximately 8 minutes. Over a 24 h period this peak grew in intensity while the peaks corresponding to the starting glycine and intermediate α-amino-β-hydroxyadipic acid methyl ester decreased. After 24 hr, the ratio of the new peak to glycine and the ester was 38:47:15. The structure of the compound corresponding to the new peak was determined to be L-erythro-α-amino-β-hydroxyadipic acid (R= $CH_2$—$CH_2$—$CO_2H$) by an independent synthesis and co-injection of the authentic product with that produced enzymatically. The chemical synthesis of the authentic material was accomplished by the aldol condensation of succinic semialdehyde methyl ester with a boron enolate of a chiral oxazine (Reno, D. S.; Lotz, B. T.; Miller, M. J. *Tetrahedron Lett.* 1990, 31, 827), followed by deprotection and hydrolysis to give the described compound.

The formation of this parent amino acid during the enzymatic synthesis occurs by hydrolysis of the initially produced amino acid monomethyl ester. Since the product has an additional ionized carboxylic acid group it is not a substrate for the enzymatically reversible aldol condensation. Thus, the novel amino acid product (L-erythro-α-amino-β-hydroxyadipic acid) accumulates. As a dicarboxylic acid amino acid product, it can be purified from the reaction mixture by ion exchange chromatography (Greenstein, J. P., Winitz, M., "Chemistry of the Amino Acids" Vol 2, pp 1452-1460, Wiley, New York, N.Y. 1961).

EXAMPLE 4

α-Amino-β-hydroxyadipic acid mono-isopropyl ester

Glycine (26.1 mg, 0.348 mmole) was dissolved in 10.0 mL of buffer and succinic semialdehyde isopropyl ester 34 mg (containing DMSO as a contaminant carried over from its preparation) was added. The presence of DMSO in the incubation has no deleterious effect on the enzyme or the reaction. The concentration of aldehyde in the buffer, after accounting for the DMSO present, was 18 mmolar. The initial concentrations of glycine and aldehyde in the incubation mixture were 17.4 mM and 9 mM respectively.

The substrate mixture (100 μL) was added to a solution of SHMT (0.1 mg) in 100 μL buffer and to the enzyme blank.

Aliquots were taken at incubation times of 0.5, 1.0, 2.0, 4.0, 6.0, 17.25, 25, and 52 hours and examined by HPLC. The main product peak (L-erythro) appeared at $T_R$ 25 min. within 0.5 h and grew to a maximum at 2-4 hours.

EXAMPLE 5

α-Amino-β-hydroxypimelic acid monomethyl ester

Glutaric semialdehyde methyl ester used in this incubation contained DMSO in a ratio of about 1:1 by weight. The DMSO is a by-product from the preparation of the aldehyde by ozonolysis of 1-methoxycyclopentene which included DMSO in the workup, (Cline, D. L. J.; Russel, C. G., Tetrahedron, 1980, 36, 1399). The substrate solution was prepared by dissolving glycine (25.6 mg, 0.341 mmol) and the aldehyde/DMSO mixture (66.7 mg) in 10.0 mL buffer to give concentrations of glycine and aldehyde of 34.1 and ~25 mM.

The enzyme solution consisted of 0.1 mg SHMT dissolved in 40 μL of buffer rather than 100 μL. The substrate solution (40 μL) was added to the enzyme and blank solutions and incubated as usual. Aliquots (10 μL) were taken at 0.5, 1.0, 1.5, 2.0, 3.0, 4.0, and 17.0 hours. By 0.5 h an enzyme-produced peak appeared in the HPLC at 23.7 min corresponding to the desired product and integrating to about 20% yield. A second small enzyme-induced peak appeared with a retention time of 22.3 min which may correspond to a minor amount of the threo isomer.

EXAMPLE 6

α-Amino-β-hydroxy-γ-oxovaleric acid

βGlycine (25.5 mg, 0.340 mmol) and pyruvaldehyde (61.1 mg of a 40 wt % solution, 0.327 mmol pyruvaldehyde) were dissolved in 10 mL buffer, pH 7.2, to give concentrations of 34 mM (glycine) and 32.7 mM (pyruvaldehyde) in the stock solution. Sodium metavanadate (1.5 mg of 90% pure compound from Aldrich) was added. After about 30 minutes it had dissolved, giving a concentration of 1.11 mM.

To the enzyme solution (0.1 mg SHMT in 80 μL) was added 80 μL of the substrate solution. Aliquots (10 μL) were removed at incubation times of 0.5, 1.0, 2.0, 3.0, 5.0, 29, and 53 hours.

Amino acid analysis by HPLC indicated the new amino acid with a retention time of 8.5 min. To confirm that this was the desired amino acid, authentic racemic material was prepared by the copper glycinate procedure. Thus, 4.23 g of copper (II) glycinate (20 mmole) was dissolved in 10 mL of 9μM aqueous KOH. Pyruvaldehyde (16.2 mL of a 40 wt % solution in water, corresponding to 7.0 g, 9.71 mmole of aldehyde) was added. After 5.25 hours, 3M $NH_4OH$ (40 mL) was added to the resulting brown solution and the solvents were evaporated to give a brown oil. The oil was passed through a column of Dowex-50 ($\oplus NH_4$ form), eluting with water to give the semipurified amino acid.

EXAMPLE 7

α-Amino-β-hydroxy-6-formyloxyhexanoic acid

The aldehdye in this incubation still retained a significant amount of DMSO from its preparation by ozonolysis of dihydropyran followed by a workup with DMSO. To 10.0 mL of buffer was added O-formyl 4-hydroxybutanal (39.5 mg, about 0.20 mmol, allowing for DMSO) and glycine (25.5 mg, 0.340 mol).

The substrate solution (40 μL) was added to the enzyme solution (0.1 mg SHMT in 40 μL) and the blank solution. Concentrations of the two substrates in the incubation mixture were 17 mM (glycine) and 10 mM (aldehyde). Aliquots (10 μL) were taken at 0.5, 1.0, 2.0, 3.0, 7.0, and 24 hours incubation time.

From the first aliquot taken at 0.5 h, two new amino aids were noted upon amino acid analysis. A small peak appeared at 15.6 min, just after the glycine peak. The other was a large, sharp peak at 22.5 minutes. By three hours, the peak at 22.5 minutes, corresponding to the expected amino acid reached a maximum at about 10% of the glycine peak and then slowly decreased while the peak at 15.6 minutes increased slightly in intensity. The amino acid eluting at 15.6 min is the product from slow hydrolysis of the formate ester in the reaction medium. The structure corresponds to α-amino-β-hydroxy-6-hydroxyhexanoic acid.

EXAMPLE 8

β-Phenylserine

The buffer solution used contained PLP in 160 μM concentration instead of 80 μM. Benzaldehyde was distilled immediately prior to use. The buffer solution was deoxygenated by bubbling nitrogen through it before adding substrates. This was to minimize the chance of the benzaldehyde being oxidized while in solution.

In 10.0 mL of buffer was dissolved glycine (25.4 mg, 0.338 mmol) and benzaldehyde (35 μL, 0.344 mmol). This solution (100 μL) was added to 100 μL of the SHMT solution (0.1 mg enzyme). Aliquots were taken at incubation times of 1.0, 5.25, and 7.0 hours.

Two product peaks were seen in the chromatograms, the larger one at 24.8 minutes and the smaller one at 23.7 minutes. The product mixture from this experiment was compared to authentic, racemic, commercially available, -phenylserine. The peaks from the two mixtures coincided exactly. Also, when compared by coinjection with authentic threo β-phenylserine, the earlier (smaller) peak was enhanced relative to the later one. These results indicate that the enzyme is producing both pairs of enantiomers of the aromatic amino acids, but favors the erythro isomers.

EXAMPLE 9

α-Amino-β-hydroxy-β-(2-furyl)propionic acid

The 2-furfural used in this example was prepared by two distillations over sodium carbonate with the second distillation under a nitrogen atmosphere. The distilled aldehyde was stored, prior to use, dessicated, under nitrogen and protected from light.

The substrate solution was prepared by dissolving glycine (14.0 mg, 0.186 mmol) and furaldehyde (15.5 μL, 0.187 mmol) in buffer (10.0 mL). When 360 μL of this was added to the enzyme solution (0.2 mg SHMT in 40 μL), the concentration of each substrate was 17 mM.

Aliquots (10 μL) were removed at 1.0, 2.0, 4.0, 5.0, 18, 24, 72, and 114 hours. Within 1 hour, two new amino acids were produced as determined by HPLC analysis. The larger peak corresponding to one isomer had a retention time of 21-22 min while the smaller peak (<50% of the larger peak) corresponding to the other (threo) isomer had a retention time of 19-20 min.

EXAMPLE 10

α-Amino-β-hydroxy-6-(2-furyl)valeric acid

The substrate solution was made by dissolving glycine (25.5 mg, 0.340 mmol) and the aldehyde (46.3 mg, 0.373 mmol) in 10.0 mL buffer. The aldehyde (a liquid) took about fifteen minutes to dissolve.

The substrate solution (100 μL) was added to the enzyme solution (0.1 mg SHMT in 100 μL buffer) and incubated at 37° C. Aliquots were taken at 0.55, 1.0, 2.0, 4.25, 8.0, and 21 hours. Within 0.5 hours a peak with retention time of 21.3 min in the HPLC analysis appeared indicating about 3conversion of glycine to the aldol product.

EXAMPLE 11

α-Amino-β-hydroxyhex-5-yneoic acid is obtained by following the incubation procedures described in the foregoing examples with propargyl aldehyde.

EXAMPLE 12

α-Amino-β-hydroxyhex-5-enoic acid is obtained with allyl aldehyde under the incubation conditions described in the above examples.

EXAMPLE 13

α-Amino-β-hydroxy-pent-4-enoic acid is obtained with acrolein by following the procedures and under the conditions described in the foregoing examples.

EXAMPLE 14

α-Amino-β-hydroxy-δ-cyanovaleric acid is produced under the conditions of the foregoing examples with β-cyanopropionaldehyde.

I claim:

1. A process for preparing a β-hydroxy-α-amino acid of the formula

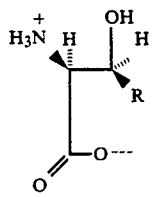

where R is ethyl substituted by esterified carboxy; which comprises mixing at a temperature of between about 30° C. and about 55° C. in an aqueous solution at a pH between about 5.5 and about 9, an aldehyde of the formula RCHO, wherein R has the same meanings as defined above, and glycine with serine hydroxymethyltransferase in the presence of pyridoxal 5'-phosphate.

2. The process of claim 1 wherein the aldehyde RCHO is succinic semialdehyde methyl ester.

3. The process of claim 1 wherein the α-amino-β-hydroxy acid is the L-erythro diastereomer.

* * * * *